United States Patent
Diab et al.

(10) Patent No.: US 9,775,546 B2
(45) Date of Patent: *Oct. 3, 2017

(54) HYPERSATURATION INDEX

(71) Applicant: MASIMO CORPORATION, Irvine, CA (US)

(72) Inventors: Mohamed K. Diab, Ladera Ranch, CA (US); Prashanth Iyengar, Irvine, CA (US); Anand Sampath, Irvine, CA (US); Ammar Al-Ali, San Juan Capistrano, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/852,356

(22) Filed: Sep. 11, 2015

(65) Prior Publication Data

US 2016/0000362 A1   Jan. 7, 2016

Related U.S. Application Data

(63) Continuation of application No. 13/865,081, filed on Apr. 17, 2013, now Pat. No. 9,131,881.

(Continued)

(51) Int. Cl.
| | | |
|---|---|---|
| *A61B 5/1455* | (2006.01) | |
| *A61B 5/00* | (2006.01) | |
| *A61B 5/0205* | (2006.01) | |

(52) U.S. Cl.
CPC ........ *A61B 5/14552* (2013.01); *A61B 5/0205* (2013.01); *A61B 5/14551* (2013.01);
(Continued)

(58) Field of Classification Search
CPC .............. A61B 5/1445; A61B 5/14551; A61B 5/14552; A61B 5/7275
See application file for complete search history.

(56) References Cited

U.S. PATENT DOCUMENTS

| | | |
|---|---|---|
| 3,734,091 A | 5/1973 | Taplin |
| 4,094,305 A | 6/1978 | Kessler |

(Continued)

FOREIGN PATENT DOCUMENTS

| | | |
|---|---|---|
| EP | 0329297 A2 | 8/1989 |
| EP | 0753320 A1 | 1/1997 |
| WO | WO 2013/158791 A3 | 10/2013 |

OTHER PUBLICATIONS

US 8,845,543, 09/2014, Diab et al. (withdrawn)
International Search Report and Written Opinion for PCT/US2013/037019 mailed Oct. 25, 2013 in 18 pages.

*Primary Examiner* — Eric Winakur

(74) *Attorney, Agent, or Firm* — Knobbe, Martens, Olson & Bear, LLP

(57) ABSTRACT

Embodiments of the present disclosure provide a hypersaturation index for measuring a patient's absorption of oxygen in the blood stream after a patient has reached 100% oxygen saturation. This hypersaturation index provides an indication of the partial pressure of oxygen of a patient. In an embodiment of the present invention, a hypersaturation index is calculated based on the absorption ratio of two different wavelengths of energy at a measuring site. In an embodiment of the invention, a maximum hypersaturation index threshold is determined such that an alarm is triggered when the hypersaturation index reaches or exceeds the threshold. In another embodiment, an alarm is triggered when the hypersaturation index reaches or falls below its starting point when it was first calculated.

19 Claims, 16 Drawing Sheets

Related U.S. Application Data

(60) Provisional application No. 61/719,866, filed on Oct. 29, 2012, provisional application No. 61/703,087, filed on Sep. 19, 2012, provisional application No. 61/625,599, filed on Apr. 17, 2012.

(52) U.S. Cl.
CPC ............ *A61B 5/7282* (2013.01); *A61B 5/743* (2013.01); *A61B 5/7405* (2013.01); *A61B 5/746* (2013.01); *A61B 5/6826* (2013.01); *A61B 2562/0238* (2013.01); *A61M 2230/205* (2013.01)

(56) References Cited

U.S. PATENT DOCUMENTS

| | | |
|---|---|---|
| 4,333,473 A | 6/1982 | Eberhard et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,184,618 A | 2/1993 | Wider et al. |
| 5,319,355 A | 6/1994 | Russek |
| 5,337,744 A | 8/1994 | Branigan |
| 5,341,805 A | 8/1994 | Stavridi et al. |
| 5,355,880 A * | 10/1994 | Thomas ............... A61B 5/1491 600/326 |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |

(56) References Cited

U.S. PATENT DOCUMENTS

| | | |
|---|---|---|
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |

(56) References Cited

U.S. PATENT DOCUMENTS

| | | |
|---|---|---|
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |

(56) References Cited

U.S. PATENT DOCUMENTS

| | | |
|---|---|---|
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 2005/0197551 A1 | 9/2005 | Al-Ali et al. |
| 2008/0097173 A1 | 4/2008 | Soyemi et al. |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0261979 A1 | 10/2010 | Kiani |
| 2010/0331639 A1 | 12/2010 | O'Reilly |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0295093 A1 | 12/2011 | Graboi et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |

(56) References Cited

U.S. PATENT DOCUMENTS

| | | |
|---|---|---|
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166210 A1 | 6/2016 | Al-Ali |

\* cited by examiner

HYPERSATURATION INDEX

PRIORITY CLAIM TO RELATED PROVISIONAL APPLICATIONS

The present application is a continuation of U.S. patent application Ser. No. 13/865,081, filed Apr. 17, 2013, entitled "Hypersaturation Index," which claims priority benefit under 35 U.S.C. §119(e) of U.S. Provisional Application Ser. No. 61/719,866, filed Oct. 29, 2012, entitled "Noninvasive Partial Pressure of Oxygen Sensing System," U.S. Provisional Application Ser. No. 61/703,087, filed Sep. 19, 2012, entitled "Noninvasive Partial Pressure of Oxygen Sensing System," and U.S. Provisional Application Ser. No. 61/625,599, filed Apr. 17, 2012, entitled "Noninvasive Partial Pressure of Oxygen Sensing System," the disclosures of which are incorporated herein by reference.

FIELD OF THE INVENTION

The present invention relates to the field of noninvasive oxygen delivery measurement using optical based sensors.

BACKGROUND

The measurement of oxygen delivery to the body and the corresponding oxygen consumption by its organs and tissues is vitally important to medical practitioners in the diagnosis and treatment of various medical conditions. Oxygen delivery is useful, for example, during certain medical procedures, where artificially providing additional oxygen to the patient's blood stream may become necessary. For example, during an intubation procedure, the patient will stop breathing while the procedure is performed. The patient is typically provided with oxygen before the intubation procedure. Because the patient stops breathing during an intubation procedure, the patient's blood oxygen saturation level will fall. In that situation, the medical practitioner must ensure that the patient has sufficient reserves of oxygen in their system before intubation so that during the intubation procedure suffocation is avoided. At the same time, providing oxygen at a high pressure to a patient can cause damage to the alveoli of an adult patient. On the other hand, even normal oxygen levels can or cause blindness in neonatal patients.

The current standard of care is to measure oxygen delivery through the use of a pulse oximeter. Pulse oximeters measure oxygen saturation ($SpO_2$). $SpO_2$ represents the percent of available hemoglobin that can chemically bind with oxygen molecules.

Another indicator of oxygen delivery is the partial pressure of oxygen ($PaO_2$), However, there are currently no reliable ways to measure $PaO_2$ noninvasively. Invasive $PaO_2$ measurements require expensive sensors and are known to carry serious side effects that can harm the health of a patient.

SUMMARY

Embodiments of the present disclosure provide a hypersaturation index for measuring a patient's absorption of oxygen in the blood stream after a patient has reached 100% oxygen saturation. This hypersaturation index provides an indication of an increased level of dissolved oxygen in the plasma. This is useful, for example, for patients that are on supplemental oxygen therapy or are on a ventilator or closed-loop positive pressure delivery device. An excessively high level of $PaO_2$ can be dangerous for most patients. In some patients, for example neonates, a high level of $PaO_2$ can cause loss of eyesight. Significant damage can occur to the lungs, and in particular, to the alveoli structures in the lungs, if the $PaO_2$ level is too high.

In another embodiment, a timer is provided that indicates when a hypersaturated patient is likely to return to a baseline saturation level after oxygen administration is stopped. This is useful, for example, during an intubation procedure.

Pulse oximetry is a noninvasive technique which allows the continuous in vivo measurement of arterial oxygen saturation and pulse rate in conjunction with generation of a photoplethsymograph waveform. Measurements rely on sensors which are typically placed on the fingertip of an adult or the foot of an infant. As explained in detail below, the ratio of red and infrared light signals absorbed at the measuring site is calculated (R/IR ratio). Oxygen saturation level is determined using a lookup table that is based on empirical formulas that convert the ratio of red and infrared absorption rates to a $SpO_2$ value.

A correlation exists between the R/IR ratio and the level of $PaO_2$. This relationship between R/IR ratio and $PaO_2$ levels, however, varies from patient to patient. For example, at the same $PaO_2$ level, one patient may have a R/IR ratio of 0.55 and another patient may have a reading of 0.45. Therefore, once the absorption level reaches 100%, it becomes difficult for the medical practitioner to assess the patient's condition with respect to $PaO_2$ and the potential dangers of a high level of $PaO_2$. Without the ability to accurately measure the $PaO_2$ level, medical practitioners are in need of a noninvasive way to monitor a patient's hypersaturation status.

In an embodiment of the present invention, a hypersaturation index is calculated based on the reading of the R/IR ratio at the measurement site. In an embodiment of the invention, a maximum hypersaturation index threshold is determined such that an alarm is triggered when the hypersaturation index reaches or exceeds the threshold. In another embodiment, an alarm is triggered when the hypersaturation index reaches or falls below its starting point when it was first calculated.

BRIEF DESCRIPTION OF THE DRAWINGS

The drawings and following associated descriptions are provided to illustrate embodiments of the present disclosure and do not limit the scope of the claims. Corresponding numerals indicate corresponding parts, and the leading digit of each numbered item indicates the first figure in which an item is found.

DETAILED DESCRIPTION

Aspects of the disclosure will now be set forth in detail with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit the scope of the disclosure herein, which is instead defined by the claims following this description.

Figure 1:
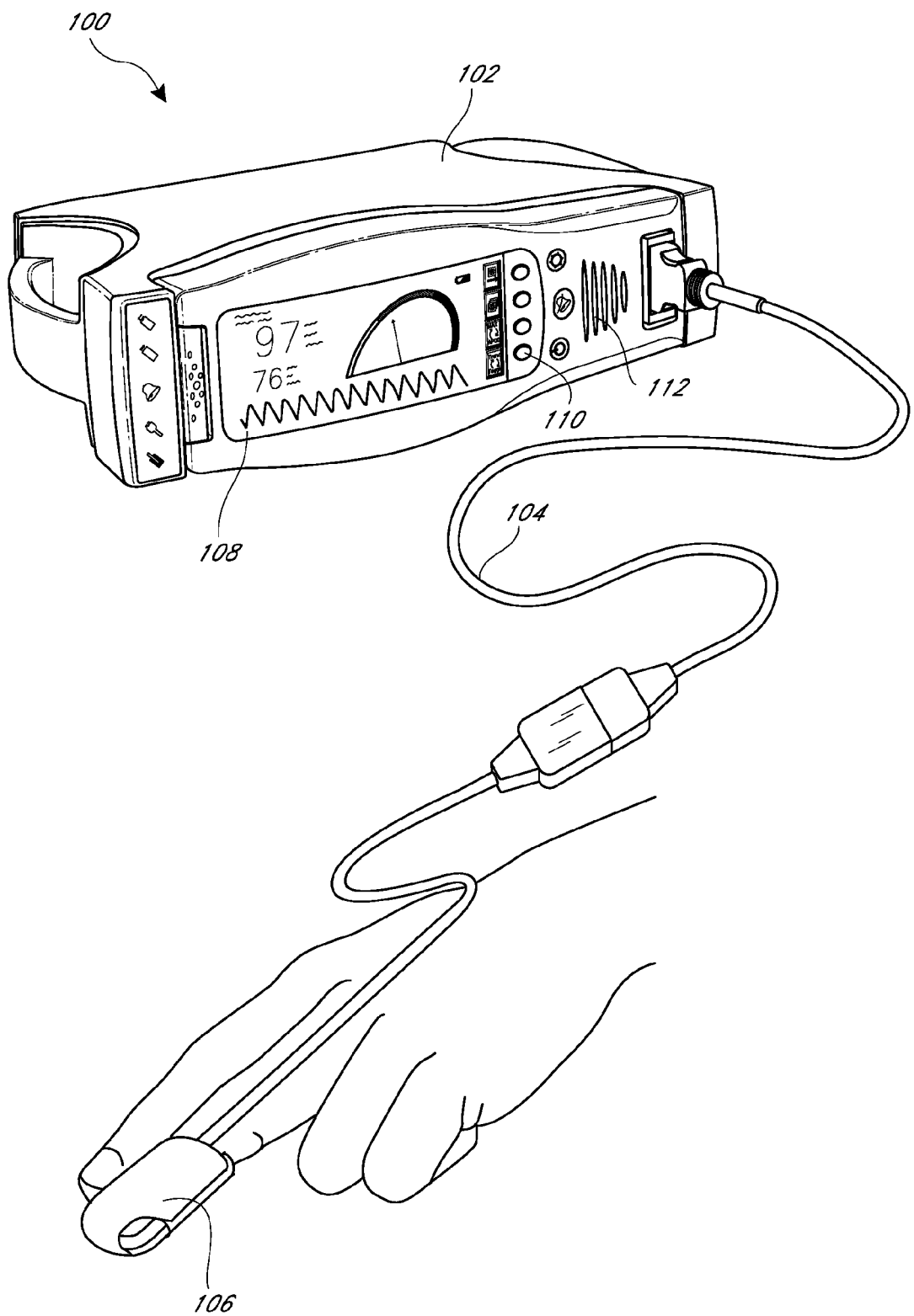
FIG. 1 illustrates a perspective view of a patient monitoring system in accordance with an embodiment of the disclosure.

Turning to FIG. 1, a patient monitoring system 100 is illustrated. The patient monitoring system 100 includes a patient monitor 102 attached to a sensor 106 by a cable 104. The sensor monitors various physiological data of a patient and sends signals indicative of the parameters to the patient monitor 102 for processing. The patient monitor 102 generally includes a display 108, control buttons 110, and a speaker 112 for audible alerts. The display 108 is capable of displaying readings of various monitored patient parameters, which may include numerical readouts, graphical readouts, and the like. Display 108 may be a liquid crystal display (LCD), a cathode ray tube (CRT), a plasma screen, a Light Emitting Diode (LED) screen, Organic Light Emitting Diode (OLED) screen, or any other suitable display. A patient monitoring system 102 may monitor oxygen saturation (SpO2), hypersaturation, perfusion index (PI), pulse rate (PR), hemoglobin count, and/or other parameters.

Figure 2:
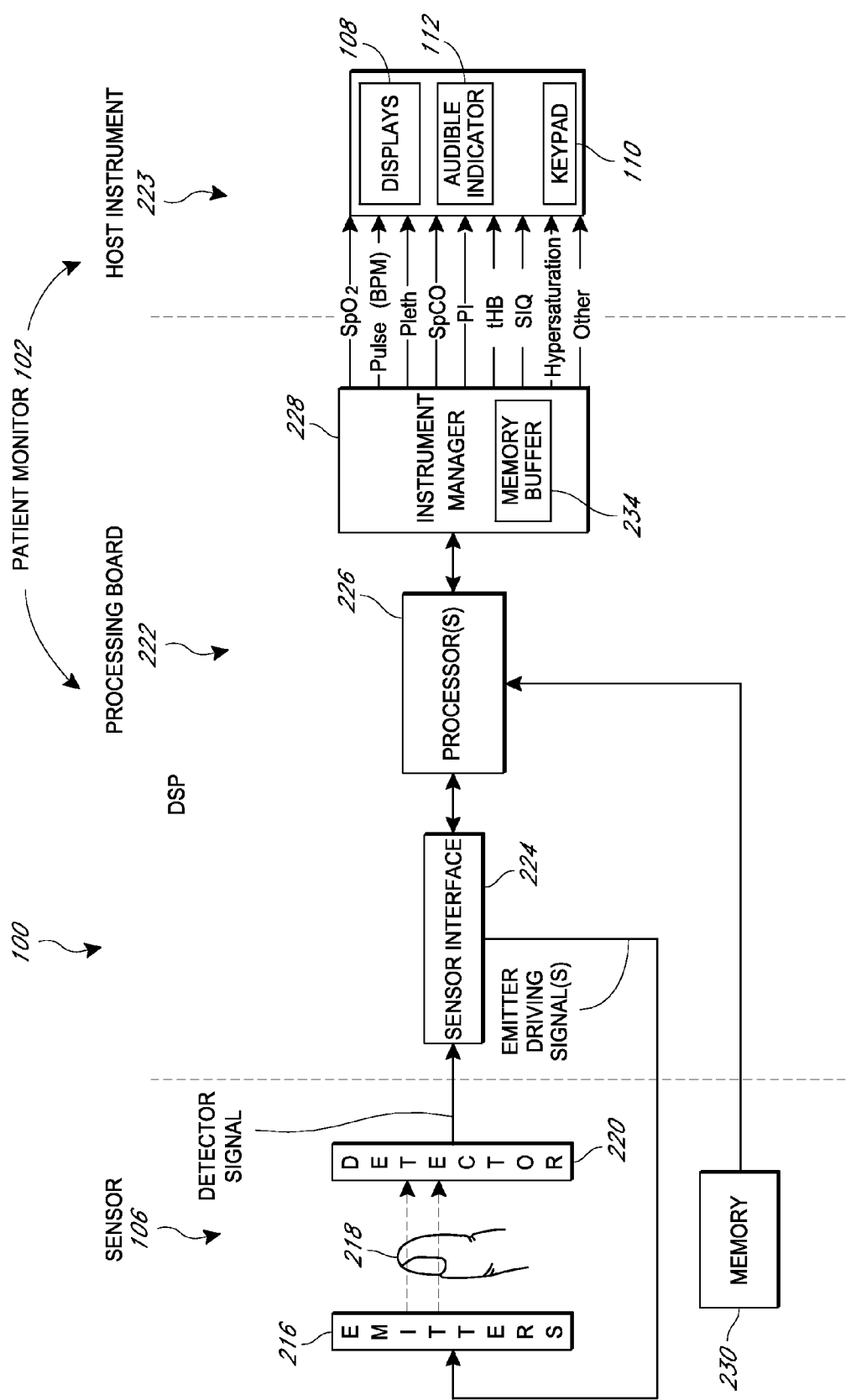
FIG. 2 illustrates a block drawing of a patient monitoring system in accordance with an embodiment of the disclosure.

FIG. 2 illustrates details of a patient monitoring system 100 in a schematic form. Typically a sensor 106 includes energy emitters 216 located on one side of a patient monitoring site 218 and one or more detectors 220 located generally opposite. The patient monitoring site 218 is usually a patient's finger (as pictured), toe, ear lobe, or the like. Energy emitters 216, such as LEDs, emit particular wavelengths of energy, typically red and infrared light signals, through the flesh of a patient at the monitoring site 218, which attenuates the energy. The detector(s) 220 then detect the attenuated energy and send representative signals to the patient monitor 102 for processing. The patient monitor 102 includes processing board 222 and a host instrument 223. The processing board 222 includes a sensor interface 224, signal processor(s) 226, and an instrument manager 228.

The host instrument typically includes one or more displays 108, control buttons 110, a speaker 112 for audio messages, and a wireless signal broadcaster 234. Control buttons 110 may comprise a keypad, a full keyboard, a track wheel, and the like. A patient monitor 102 can include buttons, switches, toggles, check boxes, and the like implemented in software and actuated by a mouse, trackball, touch screen, or other input device.

The sensor interface 224 receives the signals from the sensor 106 detector(s) 220 and passes the signals to the processor(s) 226 for processing into representations of physiological parameters. These are then passed to the instrument manager 228, which may further process the parameters for display by the host instrument 223. The processor(s) 226 may also communicate with a memory 230 located on the sensor 106; such memory typically contains information related to the properties of the sensor that may be useful in processing the signals, such as, for example, emitter 216 energy wavelengths. The elements of processing board 222 provide processing of the sensor 106 signals. Tracking medical signals is difficult because the signals may include various anomalies that do not reflect an actual changing patient parameter. Strictly displaying raw signals or even translations of raw signals could lead to inaccurate readings or unwarranted alarm states. The processing board 222 processing generally helps to detect truly changing conditions from limited duration anomalies. The host instrument 223 then is able to display one or more physiological parameters according to instructions from the instrument manager 228, and caregivers can be more confident in the reliability of the readings.

Physiology Background

When oxygen molecules come into contact with blood, the majority of the oxygen molecules are bound to the hemoglobin in red-blood cells and a small portion is dissolved directly in the blood plasma. Both of these processes are driven by the partial pressure of oxygen. In the lung, oxygen diffuses across the alveolar membrane, and then the red cell membrane in lung capillaries. When an oxygen molecule encounters a molecule of hemoglobin, it wedges itself between the iron atom and a nitrogen atom attached to the globin chain. This helps to hold the heme group in place in the protein. One molecule of hemoglobin with its four heme groups is capable of binding four molecules of diatomic oxygen, $O_2$. The pigment of the oxygen loaded heme group, which is called oxyhemoglobin, is a brilliant red color. This is typically the color of arterial blood. Pressure from dissolved oxygen in plasma and in the surroundings in the red cell helps to keep the oxygen on its binding site.

As the blood circulates to the periphery, the small amount of plasma dissolved oxygen is consumed first by cells in organs and tissues, which causes a drop in the partial pressure of oxygen. This release in pressure makes available the much larger reservoir of heme-bound oxygen which begins a sequential unloading of its four oxygen molecules. At the most, under normal circumstances only 3 molecules of oxygen are unloaded. Partially or fully unloaded hemoglobin is called deoxyhemoglobin. It is a dark blue to purplish color. This is also the typical color of venous blood.

Figure 3A:
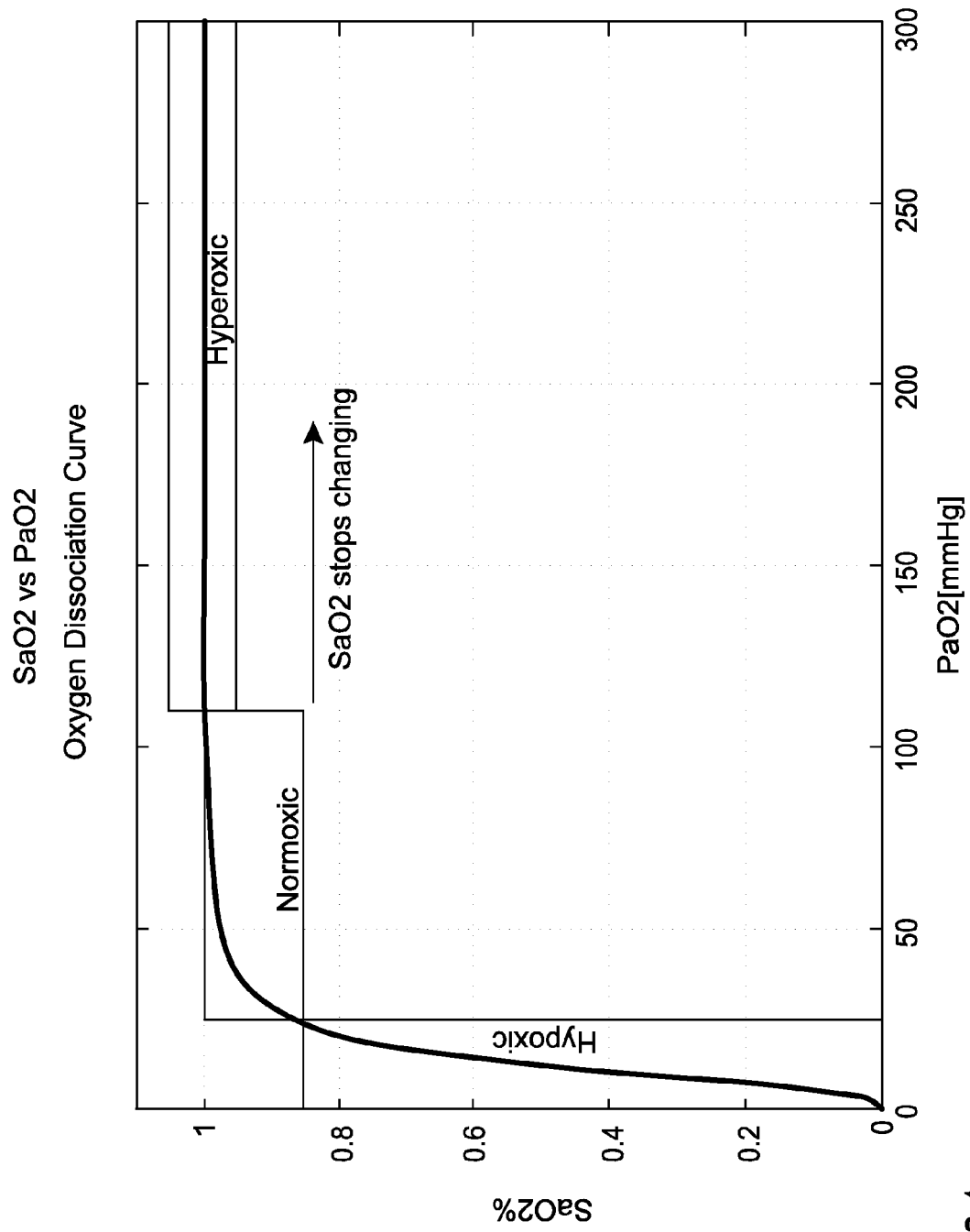
FIG. 3A-3B illustrate graphs of $SpO_2$ versus $PaO_2$.

There is a general relationship between the oxygen saturation in blood and the partial pressure of oxygen. This nonlinear relation is described by the oxygen dissociation curve as shown in FIG. 3A. FIG. 3A illustrates a graph of $SaO_2$ versus the partial pressure of oxygen dissolved in the arterial blood, $PaO_2$. As the partial pressure of oxygen in the arterial blood increases, the percentage of oxygen saturation of the hemoglobin will increase. After the $SaO_2$ level reaches 100%, the $PaO_2$ level continues to rise, but the $SaO_2$ level will not rise further. Thus, although it is possible to estimate PaO2 levels when SaO2 is below 100%, as illustrated in FIG. 3A, after a certain point, very large changes in the $PaO_2$ will produce little change in the $SaO_2$. A patient whose physiology falls on the first part of the curve is commonly referred to as the Hypoxic. As can be seen from FIG. 3A, there is a high sensitivity around $PaO_2$=30 mmHg, i.e. the slope is large. A patient whose physiology falls on the second part of the curve where $SaO_2$ begins to level off is Normoxic. In the last portion of the curve, where $SaO_2$ has reached 100%, a patient is considered Hyperoxic.

Figure 3B:
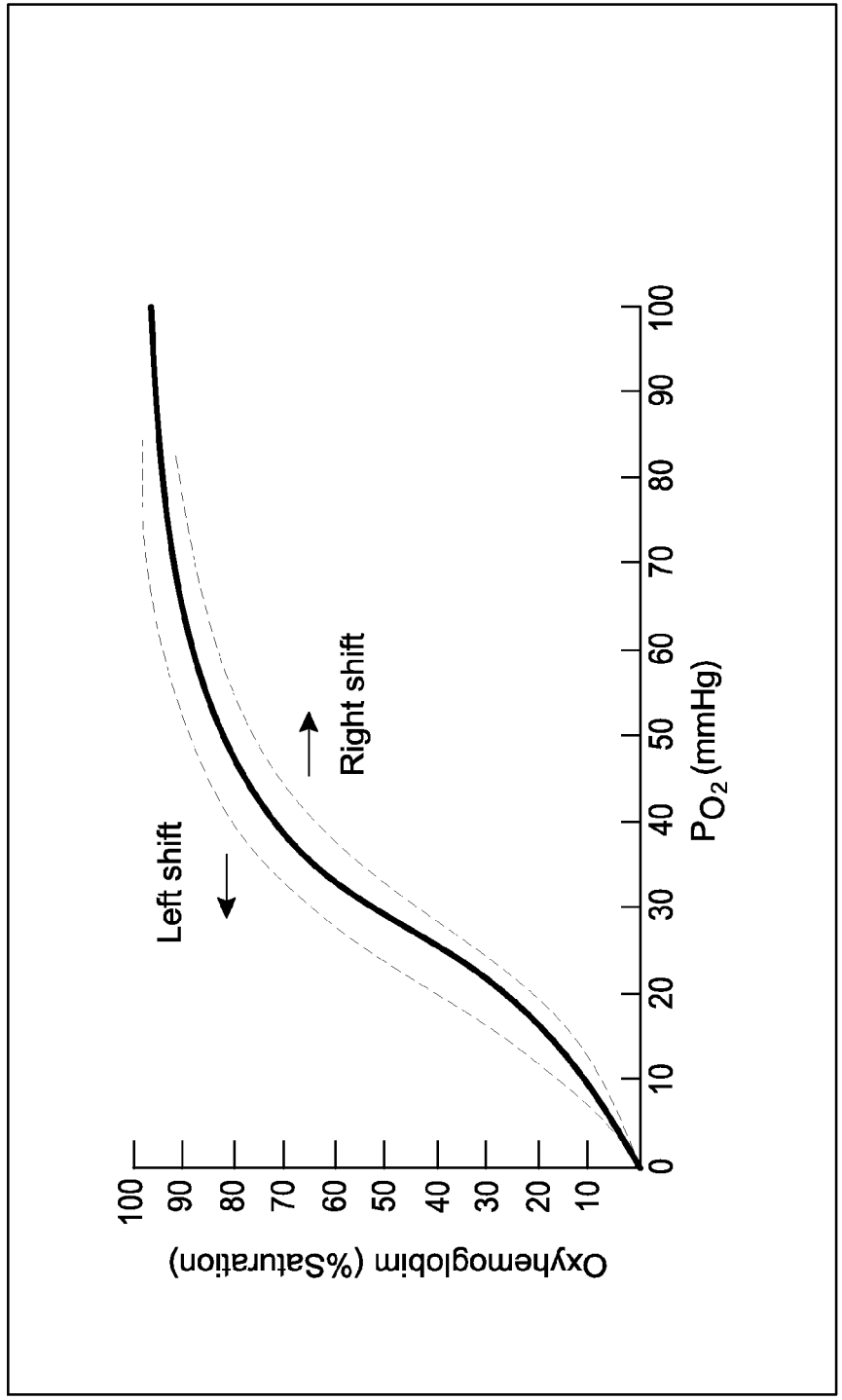

FIG. 3B illustrates a graph showing the potential shift in the disassociation curve based on an individual patients response. For example a left shift may occur with decreased temperature, decreased 1,3-diphosphoglycerate (2,30DPG), increased pH, or higher CO in the blood. As another example, a right shift will occur with reduced affinity, increased temperature, increased 2,3-DPG and decreased pH. Thus, there is some-uncertainty when determining $PaO_2$ based on the $SaO_2$ measurement. This uncertainty can be reduced if the pH and temperature are given as inputs to the device where an appropriate curve may be selected.

Oxygen Consumption

The following oxygen content equation relates the amount of oxygen present in the blood given certain hemoglobin concentration (tHb) and partial pressure of oxygen ($PaO_2$)

$$ContO_2(O_2\ mL/dL) = tHb(gramHb/dL) \cdot 1.34\ (ml\ O_2/gramHb) \cdot SaO_2 + 0.0031 (ml\ O2/mmHg/dL) \cdot PaO_2(mmHg) \quad \text{Eq. 1}$$

Alternatively, the Oxygen Content can be measured directly using a Masimo Rainbow Pulse Oximeter available from Masimo Corporation of Irvine, Calif.

Tissues need a requisite amount of O2 molecules for metabolism. Under steady state conditions the O2 consumption is fairly constant. In order to quantify the relationship between oxygen transport and its consumption the Fick principle can be applied. The essence of the Fick principle is that blood flow to an organ can be calculated using a marker substance if the following information is known:

Amount of marker substance taken up by the organ per unit time

Concentration of marker substance in arterial blood supplying the organ

Concentration of marker substance in venous blood leaving the organ

In Fick's original method, the "organ" was the entire human body and the marker substance was oxygen.

This principle may be applied in different ways. For example, if the blood flow to an organ is known, together with the arterial and venous concentrations of the marker substance, the uptake of marker substance by the organ may then be calculated.

As discussed above, hemoglobin and plasma are the main oxygen vectors in the blood. The oxygen content equation can be combined with the Fick principle to describe oxygen consumption and its relationship to blood flow as shown below in Eq.2.

$$OC = Ca[1.34 \cdot tHb \cdot (SaO2 - SvO2) + 0.0031 \cdot (PaO2 - PvO2)] \quad \text{Eq. 2}$$

Where OC is Oxygen consumption (mL/min), Ca is Cardiac output (i.e. local blood flow at the test site (dL/min)), tHb is the Total hemoglobin (gram/dL), SaO2 is Arterial saturation fraction (0-1.0), SvO2 is Venous saturation fraction (0-1.0), PaO2 is the Partial pressure of oxygen in the arterial blood (mmHg), PvO2 is the Partial pressure of oxygen in the venous blood (mmHg), 1.34 represents the HbO2 carrying capacity (mL O2/gram Hb), and 0.0031 represents O2 solubility coefficient in blood (mL O2/dL).

Noninvasive Oxygen Saturation Measurment

Figure 3C:
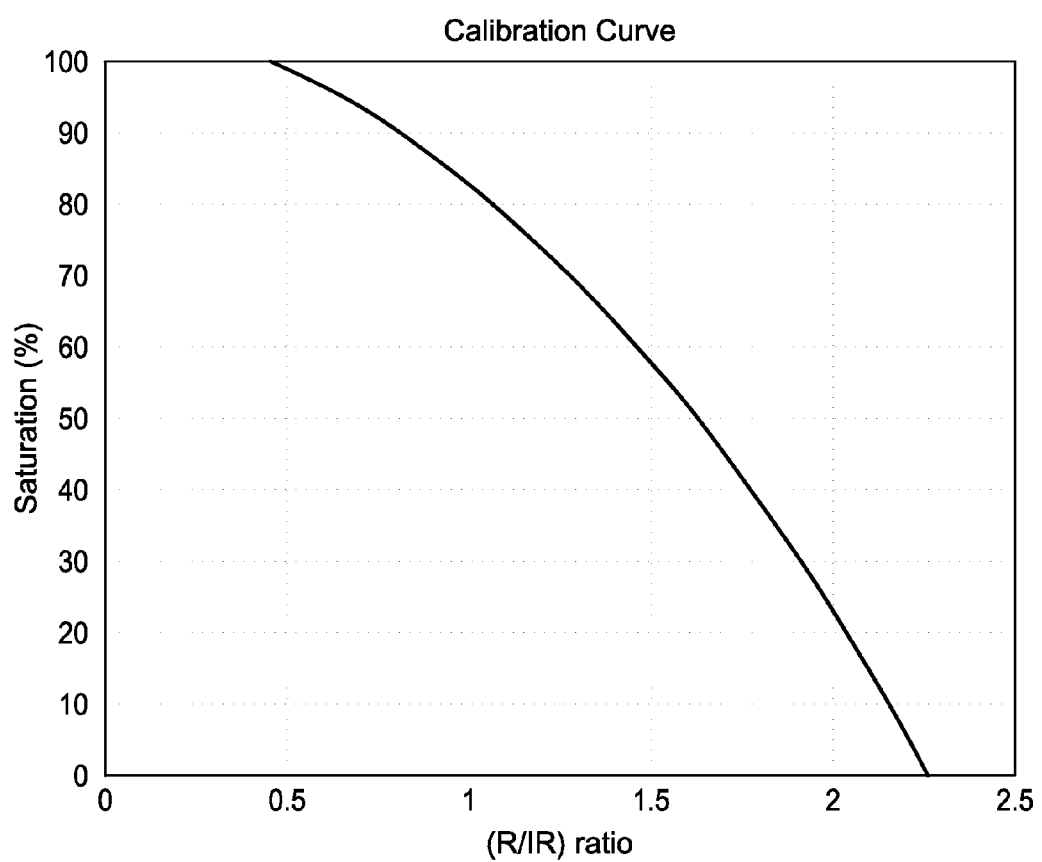
FIG. 3C illustrates a saturation calibration curve.

Pulse oximetry was invented by Dr. Ayogi in the 1972 as a technique to measure arterial oxygen saturation noninvasively. Dr. Ayogi was able to isolate the arterial pulse absorption from tissue, bone and cartilage absorptions by looking at a signal synchronous with the heartbeat reflecting the local blood flow at the measurement site. This signal is called the photo-plethysmograph and it can be isolated by the use of a high-pass filter. By exploiting the predictable relationship between arterial oxygen saturation and light absorption through a vascular bed, the arterial blood oxygen saturation ($SpaO_2$) can be calculated noninvasively. Note that the addition of a small p to $SaO_2$ to denote calculation from an arterial pulse. It can be shown that the use of two distinct light sources, Red (R)=660 nm and Infrared (IR) =910 nm, a pulse oximeter can calculate the oxygen saturation noninvasively by relating a ratio=R (AC/DC)/IR (AC/DC) to the hemoglobin oxygen saturation through a typical pulse oximeter calibration curve shown in FIG. 3C. We will refer to this ratio as (R/IR) ratio.

Modifying Eq. 2, if ($SaO_2$—$SvO_2$) is replaced with βSat, ($PaO_2$—$PvO_2$) replaced with ΔP, Ca replaced with the local blood flow (BF), the oxygen consumption is set to a constant and the equation is solved for BF, Eq. 3 results:

$$BF = Const/[1.34 \cdot tHb \cdot \beta Sat + 0.0031 \cdot \beta P] \quad \text{Eq. 3}$$

Eq. 3 shows an inverse relationship between blood flow and the arterio-venous saturation difference, ΔSat, as well as arterio-venous $O_2$ partial pressure difference (ΔP). At normal inspired oxygen levels, the majority of the oxygen is supplied by the hemoglobin. But when the concentration of inspired oxygen is raised, its partial pressure increases, hence ΔP, and more oxygen is delivered to the tissue through the $O_2$ dissolved in the plasma. Based on Eq. 3, if we consider a digit where a pulse oximeter probe is placed, the increase of inspired oxygen partial pressure will lead to a decrease in the arterio-venous ΔSat. This is true whenever the oxygen consumption is relatively constant.

Figure 3D:
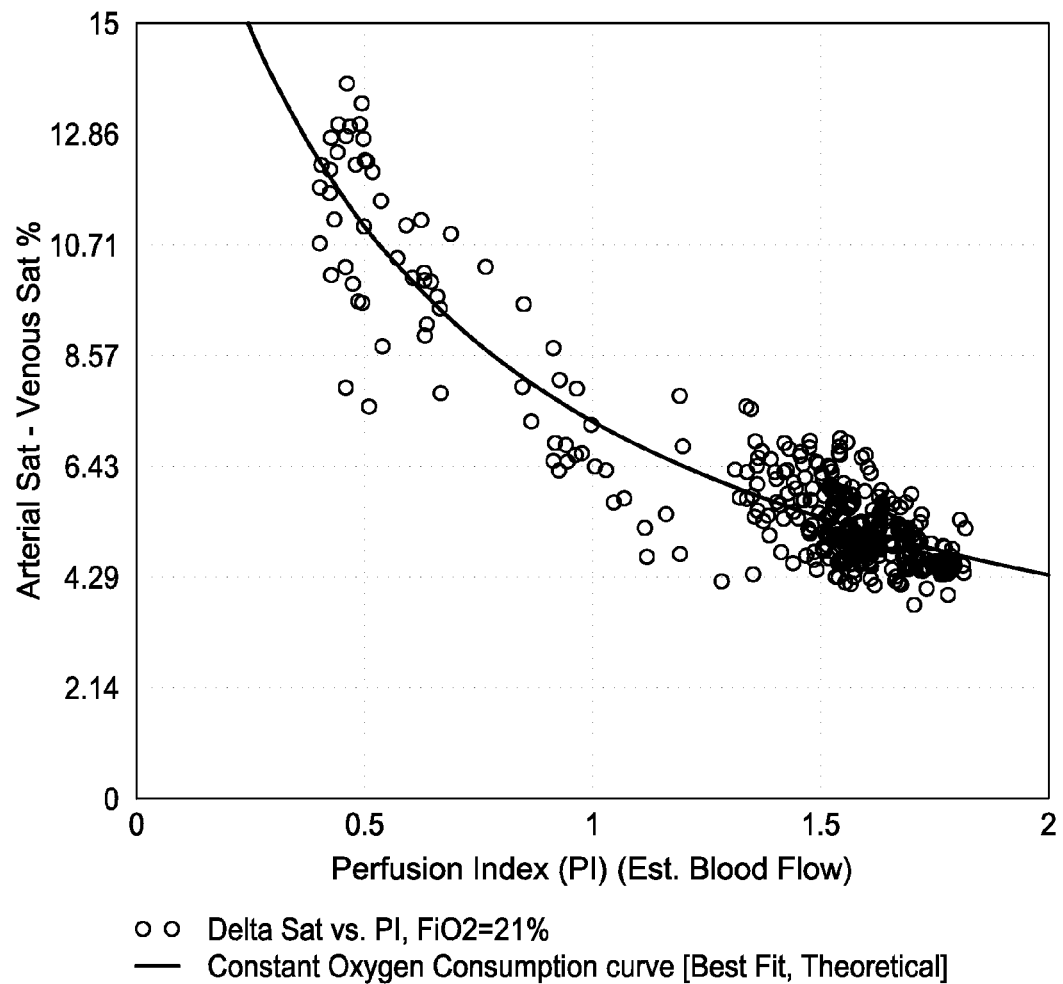
FIG. 3D-3E illustrate graphs of the difference between arterial and venous saturation vs. perfusion index.

In a vascular bed the arterial vasculature is coupled mechanically to the venous vasculature through the tissues. Although this coupling is small, the optical arterial pulse, e.g. photo-plethysmograph, has invariably a small venous component. This component is not fixed across subjects but its average is indirectly calibrated for in the saturation calibration curve. Its effect on the arterial pulse is proportional to the coupling size as well as the difference between the arterial and venous saturations at the site. Let us consider a typical subject at room-air saturation of 98%. Looking at the saturation calibration curve of FIG. 3C, a (R/IR) ratio of 0.53 corresponds to 98% saturation. If the inspired oxygen concentration is increased beyond the normal O2=21%, the (R/IR) ratio continues to drop below 0.53. An example is shown in FIG. 3F where the ratio starts at 0.43 and goes down to 0.43. It can even reach a level as low as 0.3 on some subjects at an inspired O2=100%.

This behavior may be explained by the reduction in the optical effect of venous coupling as the delta saturation between the arterial and the venous is reduced due to the increase in availability of plasma oxygen. Under this condition, the venous blood will look, optically, a lot like the arterial blood. Hence, the size of the Red photo-plethysmograph signal will shrink with respect to the IR indicating a shrinking βSat, i.e. higher venous saturation. In 1995, Masimo Corporation (Masimo) introduced a new technique for calculation the venous oxygen saturation ($SpvO_2$) by introducing an artificial pulse into the digit (see, e.g., U.S. Pat. No. 5,638,816, incorporated herein by reference). By using a pulse oximeter with a probe and a subject's digit, a continuous measure of $SpaO_2$ and $SpvO_2$ can be calculated. The blood perfusion index (PI) is used as a proxy for the blood flow to the digit. FIG. 3D depicts such an inverse relationship between blood flow (BF) and arterio-venous saturation βSat.

Figure 3E:
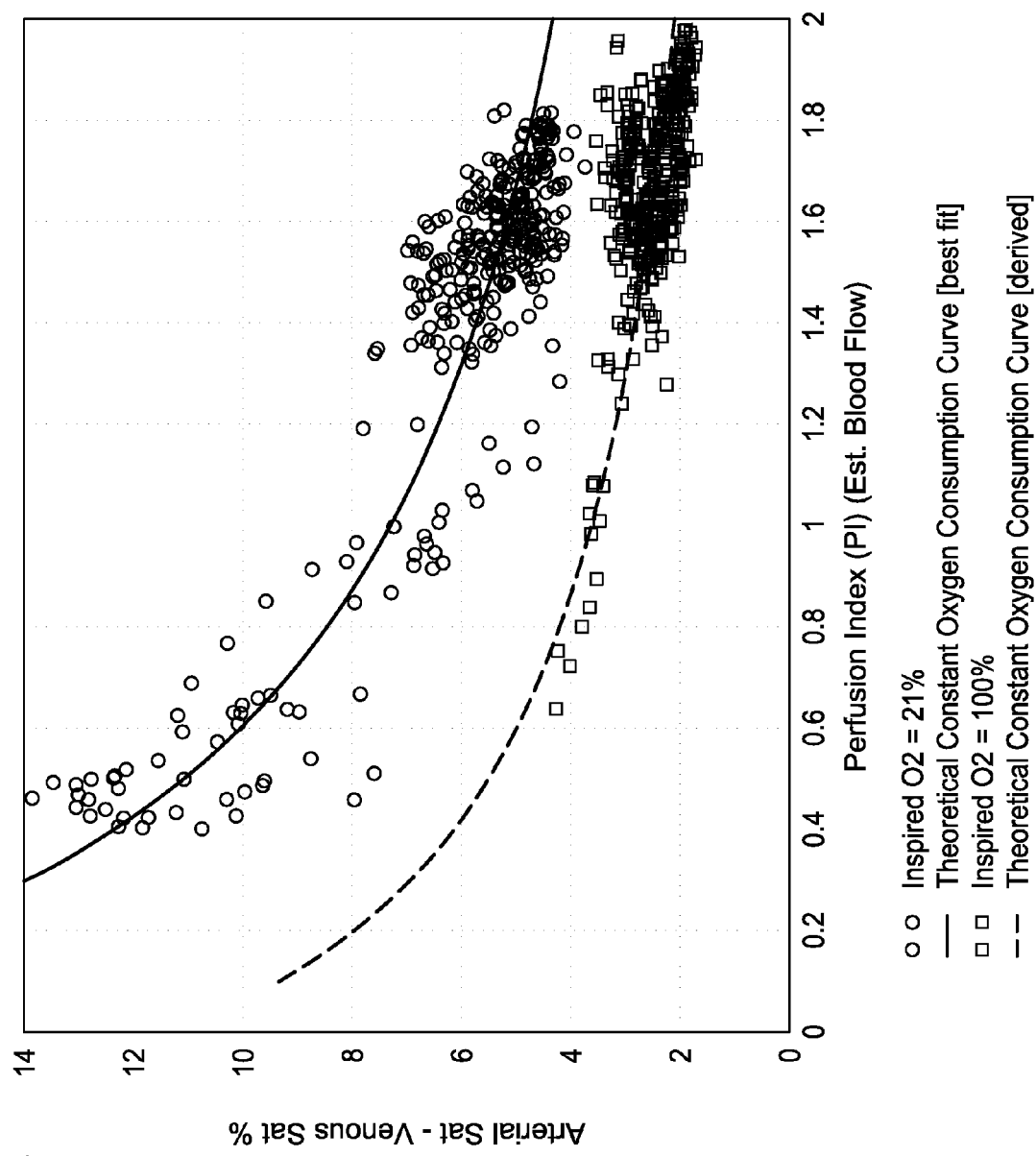
Figure 3F:
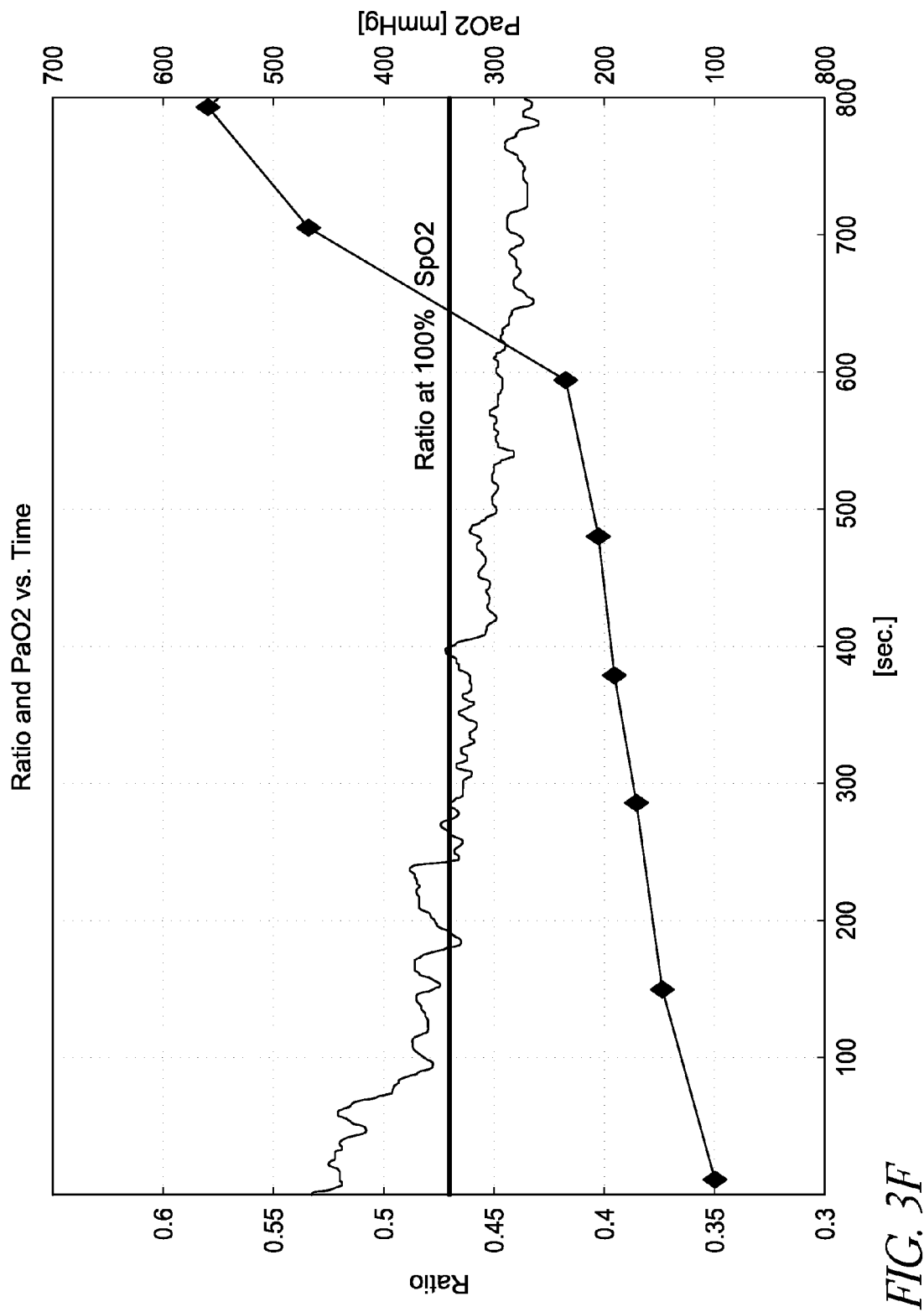
FIG. 3F illustrates the graph of the ratio of R/IR and $PaO_2$ vs. time.

FIG. 3E depicts the effect of increasing the inspired $O_2$ concentration on the calculated βSat. As expected there is a commensurate reduction in the βSat with the increase of oxygen concentration. The arterio-venous βSat will continue to decrease if the oxygen pressure is increased beyond atmospheric pressure. However, a point of diminishing return will be reached where no more change is possible. At that point the R/IR ratio will stop changing as shown in FIG. 3F. The increase in $PaO_2$ can be indirectly monitored beyond the normal 100 mmHg by looking at the effects of shrinking βSat. This cannot be done by looking at the $SaO_2$ as it will plateau at 100%.

Figure 4:
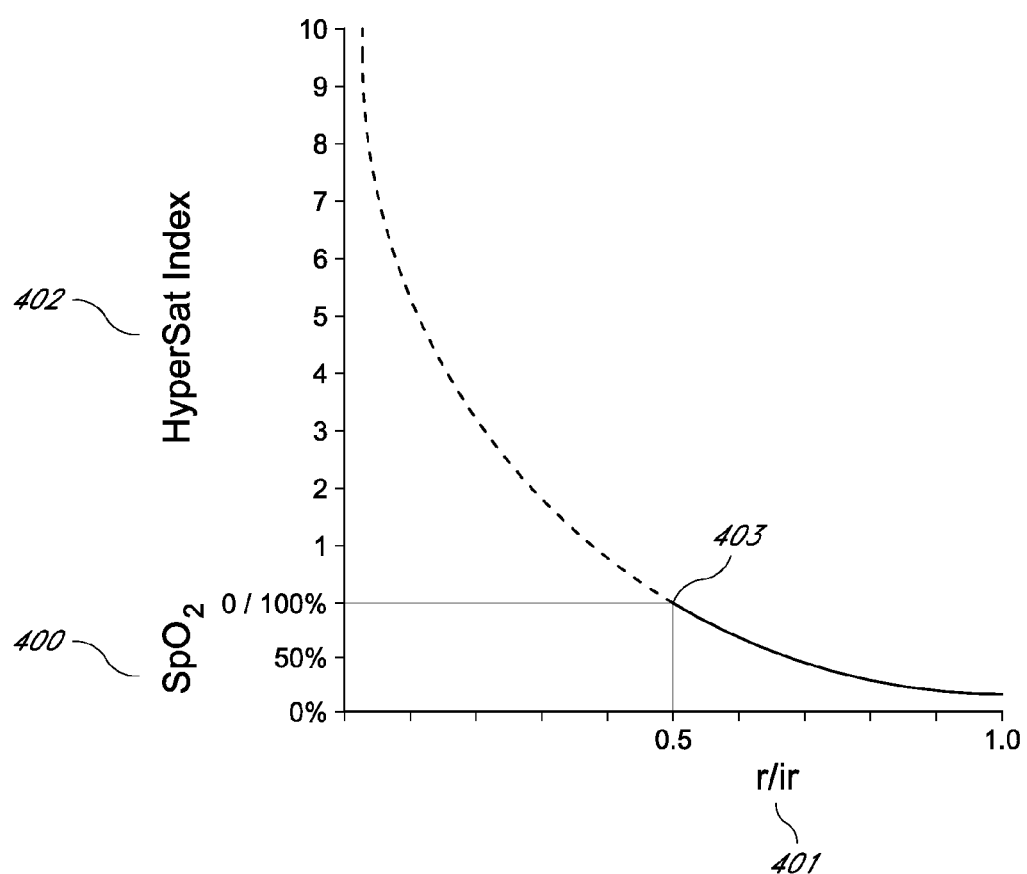
FIG. 4 illustrates a graph of $SpO_2$ versus the R/IR ratio and a hypersaturation index versus the R/IR ratio.

FIG. 4 illustrates a graph of $SpO_2$ saturation percentage 400 versus the R/IR ratio 401 according to an embodiment of the invention. In the illustrated example, the R/IR ratio is at 0.5 when the $SpO_2$ maxes out at 100%. While the $SpO_2$ level will max out at 100% saturation, the R/IR ratio continues to drop when more oxygen is dissolved in the blood. An embodiment of the invention calls for calculating a hypersaturation index 402 based on the R/IR ratio after the point 403 where the R/IR ratio translates to a $SpO_2$ level of 100% saturation. This hypersaturation index 402 assists medical practitioners in exercising their judgment in ensuring that the patient's blood is not too oversaturated with oxygen. In another embodiment, the hypersaturation index is calculated in response to a user signal, i.e., not necessarily at the point where the $SpO_2$ level is at 100% saturation.

Determining a level of hypersaturation is particularly important in a variety of patient types. For example, patients on supplemental $O_2$ titration are at risk of complications caused by hypersaturation. Patients on a ventilator or where FiO2 therapy is given to the patient are also at risk. Further, closed loop positive pressure $O_2$ delivery or $FiO_2$ delivery devices also place a patient at risk of hypersaturation. This may include, for example, CPAP machines or those suffering obstructive sleep apnea.

Figure 5:
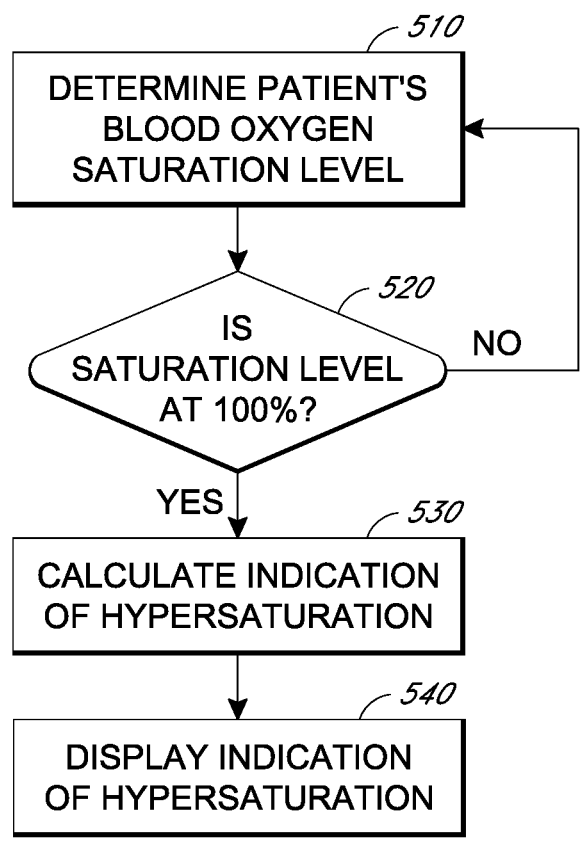
FIG. 5 illustrates a flowchart depicting an embodiment of the invention.

In an embodiment of the invention, the patient's oxygen saturation level $SpO_2$ is determined and monitored. When the saturation level reaches 100%, an indication of rising oxygen levels, such as a hypersaturation index, is calculated. The indication of rising oxygen levels may also be displayed on an output device such as the display 108 in FIG. 1. FIG. 5 is a flowchart that illustrates this embodiment of the invention. In this embodiment, the patient's blood oxygen saturation level $SpO_2$ is determined at step 500. If the blood oxygen saturation level maxes out at 100% at step 520, an indication of hypersaturation is calculated at step 530 and displayed at step 540.

Figure 6:
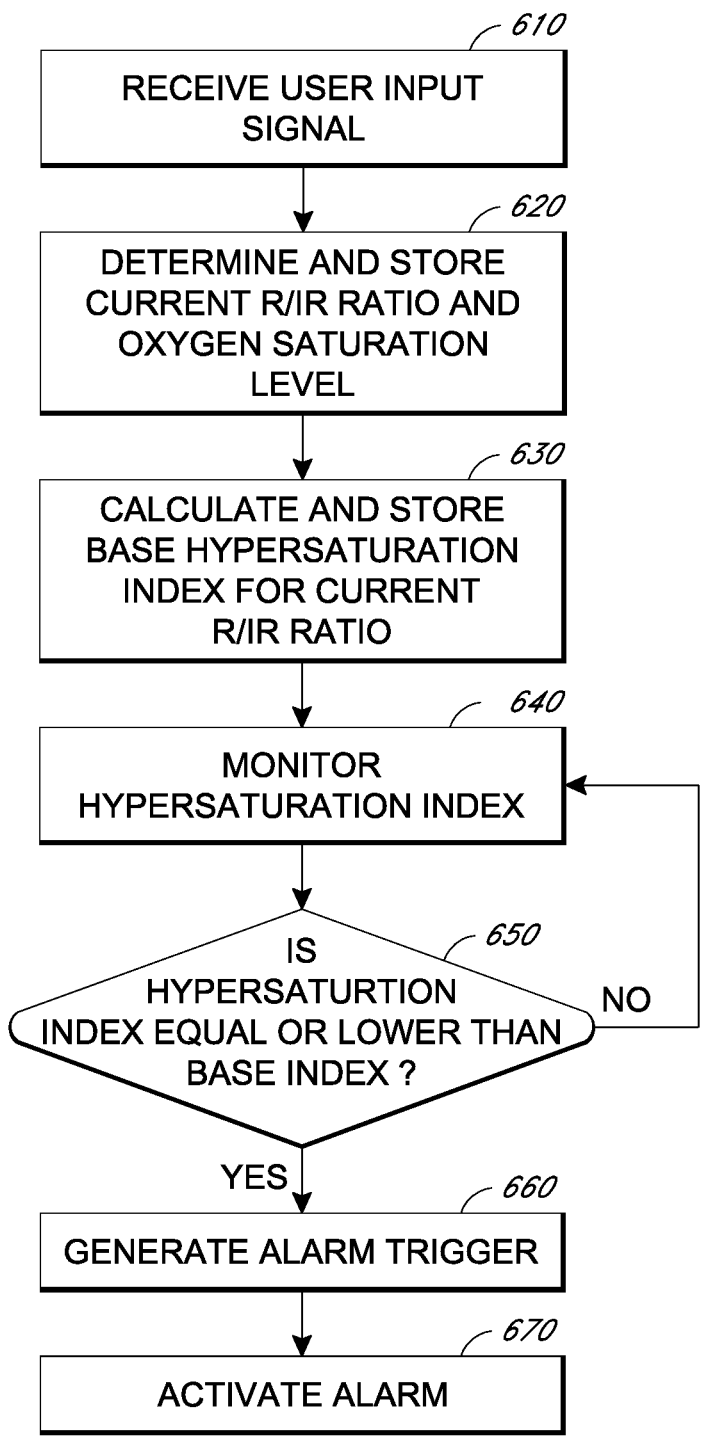
FIG. 6 illustrates a flowchart depicting an embodiment of the invention.

In another embodiment of the invention, illustrated in FIG. 6, the patient's oxygen saturation level $SpO_2$ is determined and stored at step 620 in response to a signal from the user at step 610. The signal typically indicates that a medical procedure is about to begin. A base hypersaturation index value is then calculated at step 630 based on the stored oxygen saturation level and the R/IR ratio. The hypersaturation index is then monitored at step 640 as the patient's oxygen saturation level changes. Next, an alarm trigger is generated at step 660 when the hypersaturation index value is less than or equal to the base hypersaturation index value as determined in step 650. Finally, an alarm is activated at step 670 in response to the alarm trigger.

In an alternative embodiment, the oximeter monitors a patient and automatically determines a baseline oxygen saturation level and/or baseline ratio from stable measurements taken when the oximeter first begins measurements. The oximeter can indicate that a baseline measurement has been determined or can indicate that it is unable to determine a baseline measurement if stable measurements cannot be obtained. Once a baseline measurement is obtained, the oximeter will monitor the patient for an inflection point in the saturation and ratio calculations. If the oximeter finds an inflection point where the patient's oxygen saturation begins to rise and/or ratios begin to fall, it will determine that oxygen is being administered to the patient. In this way, a caregiver is not required to push a button or otherwise indicate the start of a procedure or the start oxygen administration. Along the same lines, once a patient is hypersaturated, the oximeter will monitor the saturation level and/or ratio calculations of the patient for an inflection point indicating that oxygen is no longer being administered to the patient. Again the oximeter will alarm when the oxygen saturation values and/or ratios return to their normal baseline levels.

In yet another embodiment of the invention, a maximum hypersaturation index value is also calculated and stored in response to a user signal. In this embodiment, an alarm trigger is generated when the monitored hypersaturation index value is more than or equal to the maximum hypersaturation index value.

In an alternative embodiment, a visual oxygen hypersaturation alarm is activated. The oxygen hypersaturation alarm may include text that indicates that the oxygen hypersaturation index has dropped below the base hypersaturation index value. In another embodiment, the alarm may include text that indicates that the oxygen hypersaturation index has exceeded a threshold value. The visual oxygen hypersaturation alarm may be accompanied or replaced by an audio alarm in certain embodiments.

Figure 7:
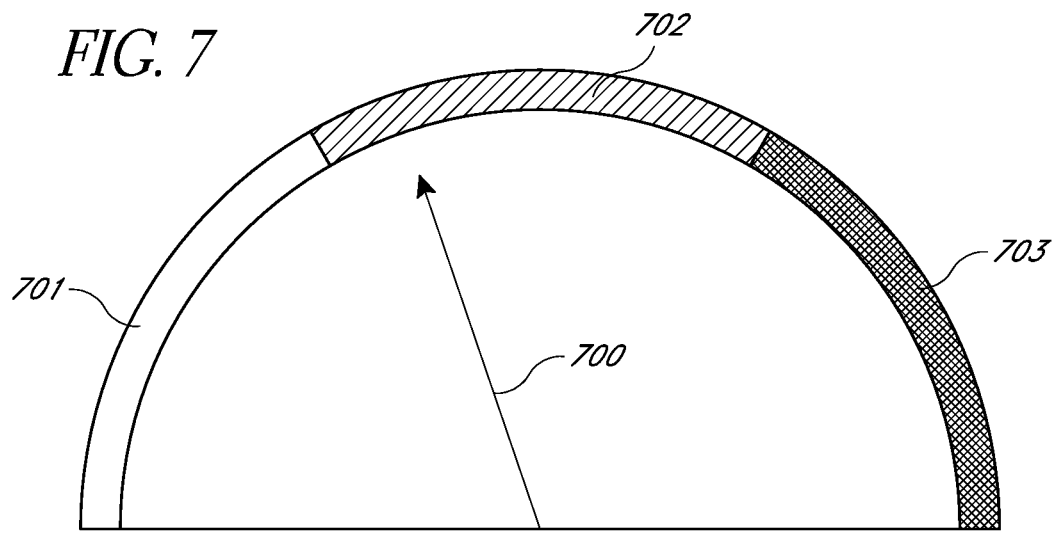
FIG. 7 illustrates a visualization of an indication of hypersaturation according to an embodiment of the invention.

FIG. 7 illustrates an example of a visualization of an indication of hypersaturation according to an embodiment of the invention. This visualization can be displayed on a display, such as the display 108 in FIG. 1. In the illustrated embodiment, the indicator is displayed as a speedometer-type visualization. The display includes a pointer 700 that points to the current value of the hypersaturation indicator. The value, for example, can be on a scale of 0-100 or 0-10 to differentiate from oxygen saturation. In one embodiment, the spectrum of possible levels may be indicated by various shades or colors. For example, the low range of values may be indicated by an area 701 that is green in color, the medium range in values may be indicated by an area 702 that is orange in color, and the high range in values may be indicated by an area 703 that is red in color.

Figure 8A:
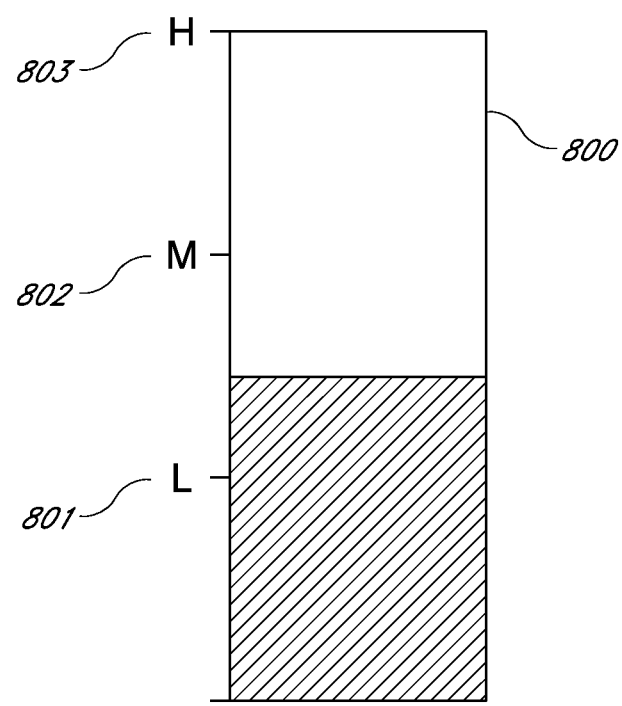
FIG. 8A-8B illustrate visualizations of indications of hypersaturation according to an embodiment of the invention.

FIG. 8A illustrates another example of a visualization of an indication of hypersaturation according to an embodiment of the invention. This visualization can also be displayed on a display, such as the display 108 in FIG. 1. In the illustrated embodiment, the hypersaturation indicator is displayed as a bar 800. In one embodiment, the size of the area of the bar that is shaded or colored depends on the value of the hypersaturation indicator. For example, a low value may be represented by a small shaded area below the "L" level 801. A medium value may be represented by a larger shaded area that remains below the "M" level 802. Finally, a high value may be represented by an even larger shaded area that can cover the entirety of the bar up to the "H" level 803.

Figure 8B:
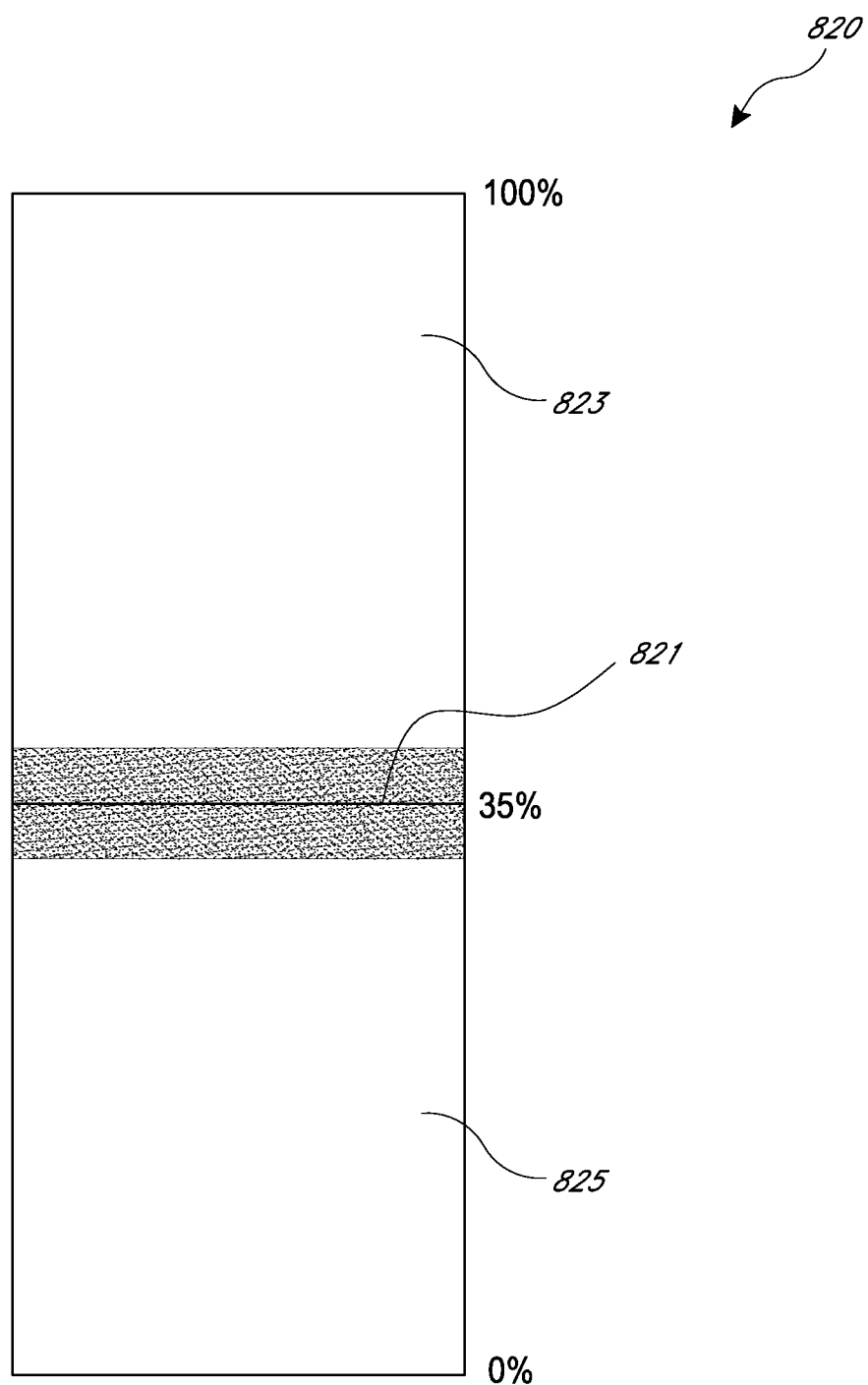

FIG. 8B illustrates yet another example of a visualization of an indication of hypersaturation. The displayed graph 820 illustrates hypersaturation on a scale of 0-100%. The line 821 illustrates an estimated hypersaturation value. The shaded area 823 illustrates the variability of the hypersaturation index. In other words, each patient's physiology is different and depending patient, their hypersaturation my not exactly follow the population average. This is explained in more detail, for example, with respect to FIG. 3B. Thus, the shaded area 823 provides an indication of the uncertainty in the estimate 821. This provides a care provider with a better indication of the actual hypersaturation that the patient is experiencing. In the embodiment of FIG. 8B, 0% represents no detectable oxygen reserve, or no indication of hypersaturation. 100% indicates a maximum detectable reserve or a maximum hypersaturation.

Figure 9A:
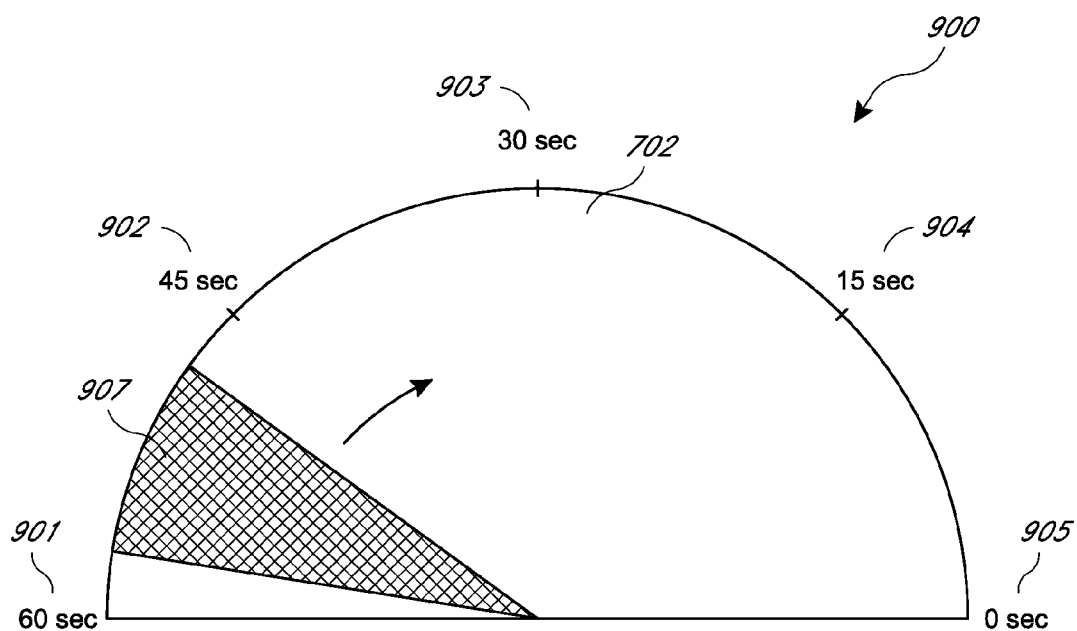
FIGS. 9A and 9B illustrate a timer display illustrating when a hypersaturated patient will return to a normal saturation level.
Figure 9B:
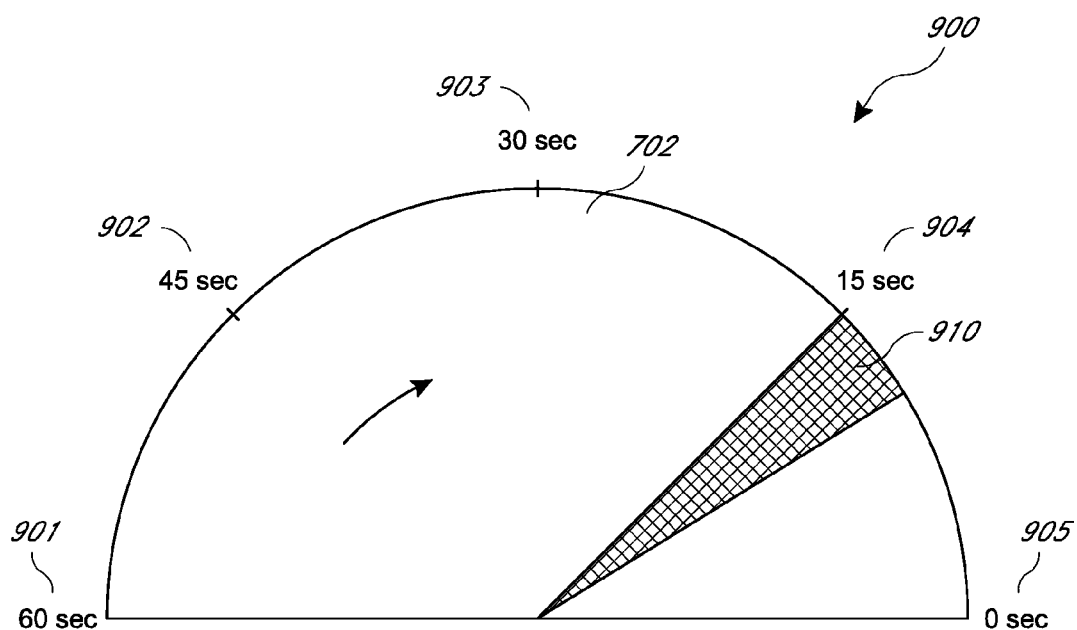

FIG. 9A illustrates an embodiment of a hypersaturation timer 900. A hypersaturation timer 900 is useful, for example, during procedures such as a patient intubation when the patient is forced to stop breathing. The timer provides an indication of the amount of time a care giver has before the patient returns from a hypersaturated state to a baseline saturation state. The timer includes a countdown indications 901-905. In the embodiment of FIG. 9A, the countdown begins at about 60 seconds and counts down to zero. When the counter is initially started, the amount of time a patient will take to return to a baseline saturation state is relatively difficult to determine. Thus, the timer 900 provides a range of time left which is illustrated by shaded area 907. The shaded area moves clockwise around the timer indicating a range of time left before the patient reaches a baseline state. As time goes by, the amount of time a patient will take to return to a baseline saturation state becomes more predictable based on how quickly the ratios change. Thus, as illustrated in FIG. 9B, the range indicated by the shaded area 910 becomes smaller.

Figure 10A:
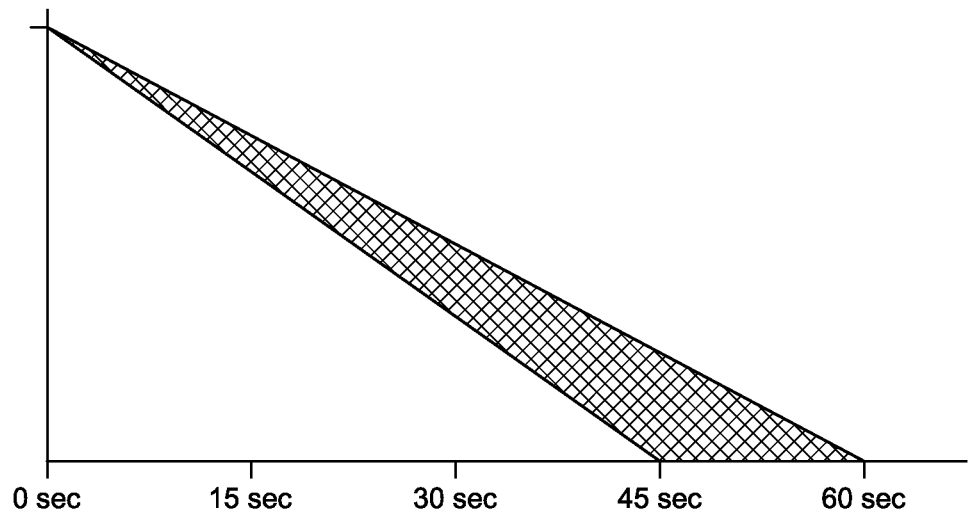
FIGS. 10A and 10B illustrate an alternative embodiment of a timer display.
Figure 10B:
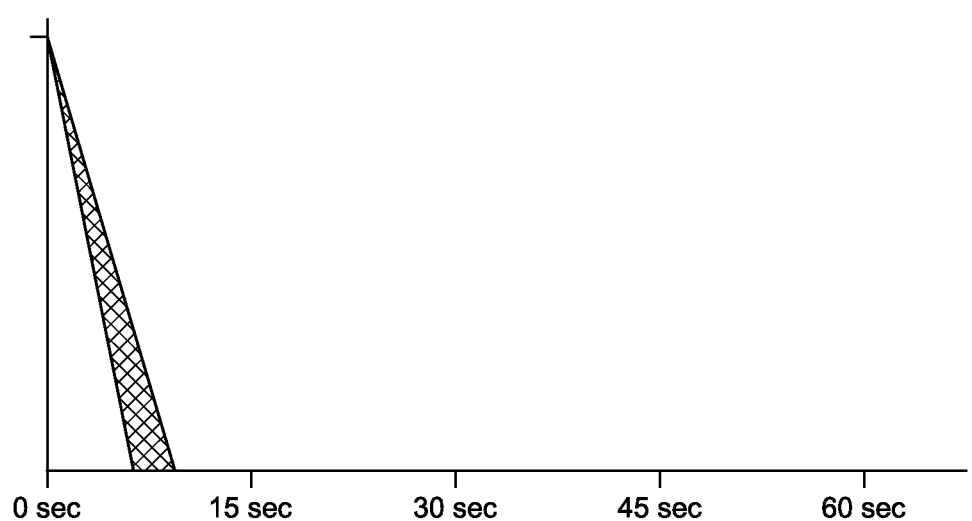

FIG. 10 illustrates another embodiment of a timer 1000. Similar to FIGS. 9A and B, timer 1000 has a count-down range 1002 that decreases as time expires and the time in which a patient returns to their base line saturation becomes more certain.

In another embodiment not shown, a simple digital count-down clock could also be used to indicate the amount of time left for a hypersaturation patient to return to their baseline saturation level. The count-down clock can indicate a range or it can simple indicate a number and speed up or slow down based on the rate of return experienced by the patient.

Figure 11:
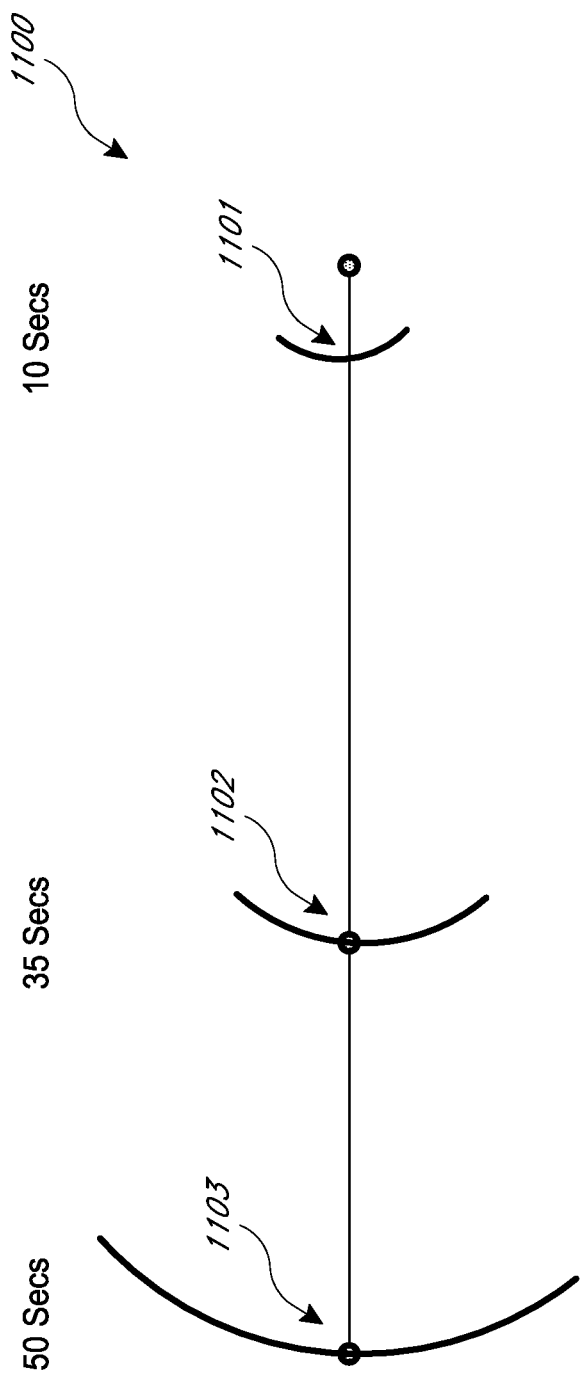
FIG. 11 illustrates another alternative embodiment of a timer display.

FIG. 11 illustrates an embodiment count down display of an oxygen reserve, or the time left for a hypersaturation patient to return to baseline saturation. Put in other terms, the time in seconds starts increasing from zero as a subject transitions from normoxia to hyperoxia. The disply then decreases when the subject transitions from the Hyperoxic state to the Normoxic state. The display of FIG. 11 includes an arc indicator, for example, arc indicators 1101, 1102, and 1103. The indicators are arced in order to show the uncertainty range in the time left in the display. Although the arcs 1101, 1102, and 1103 are all illustrated on the display for illustration and explanation purposes, it is to be understood that during measurement, only a single arc is displayed which according to the relative time Although the foregoing has been described in terms of certain specific embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions, and modifications will be apparent to the skilled artisan in view of the disclosure herein. Thus, the present disclosure is not limited by the disclosed embodiments, but is defined by reference to the appended claims. The accompanying claims and their equivalents are intended to cover forms or modifications as would fall within the scope and spirit of the disclosure.

What is claimed is:

1. A method of providing an indication of an oxygenation of blood of a non-invasively monitored patient different from oxygen saturation, wherein said oxygen saturation is a measure of a percentage of available carriers in the blood that are bound to oxygen molecules at a time of measurement acquisition, the method comprising:

using an electronic light source including one or more light emitters, emitting at least a plurality of wavelengths of light into a portion of a body of the patient;

using an electronic light detector, detecting the light after attenuation of the body, said attenuation responsive to said oxygenation of said blood, and outputting one or more signals from said light detector, said one or more signals responsive to said attenuation;

processing said one or more signals using one or more signal processors to electronically:

calculate a first index responsive to said percentage of said carriers bound to oxygen, said first index being said measure of said oxygen saturation, and calculate a second index responsive to a quantity of oxygen dissolved in the blood of a patient and not bound to any of said carriers while the patient is in a hyperoxic state, said second index providing different information to a caregiver than said first index, wherein said second index is calculated based on a ratio of information from at least a first of the plurality of wavelengths and information from at least a second of the plurality of wavelengths during the hyperoxic state of the patient; and electronically displaying at least a value responsive to said second index.

2. The method of claim 1, wherein the displaying comprises displaying an oxygen hypersaturation index.

3. The method of claim 2, wherein the hypersaturation index is indicative of the partial pressure of oxygen.

4. The method of claim 2, wherein the displaying comprises displaying a graph of the oxygen hypersaturation index.

5. The method of claim 1, wherein the displaying comprises generating an alarm in response to the value responsive to said second index crossing a threshold.

6. The method of claim 5, wherein the displaying comprises displaying an amount of time after oxygen administration is stopped until the value responsive to said second index reaches the threshold.

7. The method of claim 6, wherein the amount of time becomes more certain as time expires.

8. The method of claim 1, wherein the displayed value comprises one or more of a number, a fillable bar where a fill is responsive to said dissolved oxygen, or a color responsive to said dissolved oxygen.

9. The method of claim 1, further comprising displaying a second value responsive to said first index.

10. The method of claim 9, wherein the displayed second value comprises one or more of a numeric percentage, a fillable bar where a fill is responsive to said percentage, or a color responsive to said percentage.

11. The method of claim 1, wherein the calculating of the first and/or second indices comprises using an oxygen saturation curve, wherein the oxygen saturation stays the same within a predetermined range of an R/IR ratio.

12. A system for determining an estimate of an oxygen saturation of a patient and an additional estimate of a non-invasively measured oxygen reserve of said patient, said oxygen saturation being a measure of a percentage of available carriers in blood that are bound to oxygen molecules at a time of measurement acquisition and said oxygen reserve being oxygen dissolved in the blood of a patient during a hyperoxic state of the patient and different from an amount of dissolved oxygen corresponding to said estimate of said oxygen saturation, the system comprising:

an input of an electronic physiological monitor, said input configured to receive one or more signals responsive to light of at least a plurality of wavelengths attenuated by body tissue of the patient, said one or more signals output from a light detector configured to detect said attenuated light;

one or more physiological hardware processors of said electronic physiological monitor, the one or more processors configured to electronically:

calculate a first index responsive to said percentage of said carriers bound to oxygen, said first index being said measure of said oxygen saturation, and calculate a second index responsive to said dissolved oxygen, wherein said second index is responsive to a ratiometric calculation, said ratiometric calculation including a denominator responsive to portions of said one or more signals that were responsive to at least one of said plurality of wavelengths during the hyperoxic state of the patient and a numerator responsive to portions of said one or more signals that were responsive to at least another of said plurality of wavelengths during the hyperoxic state of the patient; and a display electronically providing at least a visual indicia of said second index.

13. The system of claim 12, wherein the displayed visual indicia of said second index is an oxygen hypersaturation index.

14. The system of claim 13, wherein the hypersaturation index is indicative of the partial pressure of oxygen.

15. The system of claim 12, wherein the displayed visual indicia of said second index comprises a graph of an oxygen hypersaturation index.

16. The system of claim 12, further comprising an alarm configured to generate an alarm indication in response to the displayed visual indicia of said second index crossing a threshold.

17. The system of claim 12, wherein said visual indicia comprises one or more of a number, a fillable bar where a fill is responsive to said dissolved oxygen, or a color responsive to said dissolved oxygen.

18. The system of claim 12, wherein the display is configured to electronically provide a second visual indicia of said first index.

19. The system of claim 18, wherein said second visual indicia comprises one or more of a numeric percentage, a fillable bar where a fill is responsive to said percentage, or a color responsive to said percentage.

* * * * *

UNITED STATES PATENT AND TRADEMARK OFFICE
CERTIFICATE OF CORRECTION

| | | |
|---|---|---|
| PATENT NO. | : 9,775,546 B2 | |
| APPLICATION NO. | : 14/852356 | |
| DATED | : October 3, 2017 | |
| INVENTOR(S) | : Mohamed Kheir Diab | |

It is certified that error appears in the above-identified patent and that said Letters Patent is hereby corrected as shown below:

Sheet 4 of 16 (FIG. 3B) at Line 1 (Y-Axis), change "Oxyhemoglobim" to --Oxyhemoglobin--.

Sheet 11 of 16 (Referral Numeral 650, FIG. 6) at Line 2, change "HYPERSATURTION" to --HYPERSATURATION--.

In Column 1 at Line 52, change "($PaO_2$),"  to --($PaO_2$).--.

In Column 2 at Line 13, change "photoplethsymograph" to --photoplethysmograph--.

In Column 2 at Line 56, change "FIG." to --FIGS.--.

In Column 2 at Line 58, change "FIG." to --FIGS.--.

In Column 3 at Line 4, change "FIG." to --FIGS.--.

In Column 5 at Line approximately 49, change "Eq.2." to --Eq. 2.--.

In Column 5 at Line 51 (approx.), change "OC=Ca[1.34" to --OC = Ca • [1.34--.

In Column 5 at Line 62, change "Measurment" to --Measurement--.

In Column 6 at Line 15, change "βSat," to --ΔSat,--.

In Column 6 at Line 20, change "BF=Const/[1.34·tHb·βSat+0.0031·βP]" to
--BF = Const / [1.34 • tHb • ΔSat + 0.0031 • ΔP]--.

In Column 6 at Line 57, change "βSat," to --ΔSat,--.

In Column 6 at Line 67, change "βSat." to --ΔSat.--.

Signed and Sealed this
Twentieth Day of February, 2018

Andrei Iancu
*Director of the United States Patent and Trademark Office*

CERTIFICATE OF CORRECTION (continued)
U.S. Pat. No. 9,775,546 B2

In Column 7 at Line 2, change "βSat." to --ΔSat.--.

In Column 7 at Line 3, change "βSat." to --ΔSat.--.

In Column 7 at Line 4, change "βSat" to --ΔSat--.

In Column 7 at Line 11, change "βSat." to --ΔSat.--.

In Column 8 at Line 66, change "my not" to --may not--.

In Column 9 at Line 44, change "disply" to --display--.

In Column 9 at Line 53, change "time" to --time.--.